US007491243B2

(12) United States Patent
Klein

(10) Patent No.: US 7,491,243 B2
(45) Date of Patent: Feb. 17, 2009

(54) METHOD OF MODIFYING A LOWER ESOPHAGUS

(75) Inventor: Dean A. Klein, North Oaks, MN (US)

(73) Assignee: Carbon Medical Technologies, St. Paul, MN (US)

( * ) Notice: Subject to any disclaimer, the term of this patent is extended or adjusted under 35 U.S.C. 154(b) by 569 days.

(21) Appl. No.: 10/280,163

(22) Filed: Oct. 25, 2002

(65) Prior Publication Data

US 2003/0161887 A1 Aug. 28, 2003

Related U.S. Application Data

(63) Continuation-in-part of application No. 10/084,240, filed on Feb. 27, 2002, now abandoned.

(51) Int. Cl.
*A61F 2/02* (2006.01)

(52) U.S. Cl. ............... 623/23.68; 623/14.13; 623/23.73

(58) Field of Classification Search ............. 623/23.68, 623/14.13, 23.73

See application file for complete search history.

(56) References Cited

U.S. PATENT DOCUMENTS

| | | | | |
|---|---|---|---|---|
| 4,803,075 | A * | 2/1989 | Wallace et al. | 424/423 |
| 5,007,940 | A * | 4/1991 | Berg | 424/423 |
| 5,026,350 | A | 6/1991 | Tanaka et al. | 604/158 |
| 5,116,387 | A * | 5/1992 | Berg | 523/113 |
| 5,158,573 | A * | 10/1992 | Berg | 523/113 |
| 5,188,617 | A | 2/1993 | Linder | 604/232 |
| 5,204,382 | A | 4/1993 | Wallace et al. | 523/115 |
| 5,336,263 | A * | 8/1994 | Ersek et al. | 424/422 |
| 5,451,406 | A * | 9/1995 | Lawin et al. | 424/423 |
| 5,792,478 | A * | 8/1998 | Lawin et al. | 424/502 |
| 5,922,025 | A | 7/1999 | Hubbard | 623/11 |
| 6,098,629 | A * | 8/2000 | Johnson et al. | 128/897 |
| 6,187,318 | B1 * | 2/2001 | Mitchell et al. | 424/735 |
| 6,190,684 | B1 * | 2/2001 | Hench et al. | 424/423 |
| 6,250,307 | B1 * | 6/2001 | Conrad et al. | 128/898 |
| 6,251,064 | B1 * | 6/2001 | Silverman et al. | 600/29 |
| 6,277,392 | B1 * | 8/2001 | Klein | 424/426 |
| 6,432,437 | B1 * | 8/2002 | Hubbard | 424/424 |
| 6,537,574 | B1 | 3/2003 | Hubbard | 424/484 |
| 6,565,550 | B1 * | 5/2003 | Klein et al. | 604/506 |
| 6,591,838 | B2 * | 7/2003 | Durgin | 128/898 |
| 7,047,980 | B2 * | 5/2006 | Milbocker | 128/898 |
| 2001/0025642 | A1 | 10/2001 | Conrad et al. | 128/848 |
| 2001/0044587 | A1 | 11/2001 | Conrad et al. | 600/742 |
| 2001/0051670 | A1 | 12/2001 | Goupil et al. | 523/113 |
| 2002/0091295 | A1 * | 7/2002 | Wilk | 600/12 |
| 2002/0151466 | A1 | 10/2002 | Hubbard et al. | 514/2 |
| 2004/0028676 | A1 * | 2/2004 | Klein et al. | 424/125 |
| 2004/0037887 | A1 * | 2/2004 | Bourne et al. | 424/486 |
| 2004/0089313 | A1 * | 5/2004 | Utley et al. | 128/898 |
| 2004/0122470 | A1 * | 6/2004 | Deem et al. | 606/213 |

FOREIGN PATENT DOCUMENTS

| | | | |
|---|---|---|---|
| DE | 346 472 | | 8/1919 |
| DE | 93 18 938 | | 2/1994 |
| DE | 197 50 090 | | 6/1999 |
| EP | 0251695 | A2 * | 1/1988 |
| EP | 1 093 767 | | 4/2001 |
| FR | 1 296 976 | | 6/1962 |
| FR | 1 501 120 | | 10/1967 |
| GB | 472 952 | | 10/1937 |
| WO | WO 01 19287 | | 3/2001 |
| WO | WO 02 00192 | | 1/2002 |
| WO | WO 02 13876 | | 2/2002 |

OTHER PUBLICATIONS

Abstract of journal article of Mason et al, "Endoscopic Augmentation of the cardia with a biocompatible polymer (Enteryx) in a porcine model", Mar. 2002, Springer Verlag, vol. 16, pp. 386-391.*

Mason et al, "Endoscopic augmentation of the cardia with a biocompatible injection polymer (Enteryx) in a porcine model", (Dec. 2001), Springer-Verlag New York Inc., 16:386-391, pp. 386-391.*

Deviere J., et al. *Endoscopic implantation of a biopolymer in the lower esophageal sphincter for gastroesophageal reflux: a pilot study*, Gastrointestinal Endoscopy, vol. 55, No. 3, Mar. 2002, pp. 335-341.

Malizia, et al. Migration and Granulomatous Reaction After Periurethral Injection of Polytef, JAMA, Jun. 22/29, 1984—vol. 251, No. 24, pp. 3277-3281.

Rupp, et al., "Endoscopic Antireflux Techniques," Experimental and Investigational Endoscopy, vol. 4, No. 2, Apr. 1994, pp. 353-368.

(Continued)

*Primary Examiner*—Paul Prebilic
(74) *Attorney, Agent, or Firm*—Faegre & Benson LLP

(57) ABSTRACT

The present invention provides a method of modifying the lower esophagus by injecting biocompatible particles in a biocompatible carrier into a submucosal tissue site of the lower esophagus of a patient. The method may be used to treat gastroesophageal reflux disease by optimizing the closing function of the lower esophageal sphincter.

20 Claims, No Drawings

OTHER PUBLICATIONS

Feretis, et al., Endoscopic implantation of Plexiglas (PMMA) microspheres for the treatment of GERD, Gastrointestinal Endoscopy, vol. 53, No. 4, 2001, pp. 423-426.

O'Connor, et al., "Endoscopic placement of collagen at the lower esophageal sphincter to inhibit gastroesophageal reflux: a pilot study of 10 medically intractable patients," Gastrointestinal Endoscopy, vol. 34, No. 2, 1988, pp. 106-112.

O'Connor et al., "An experimental endoscopic technique for reversing gastroesophageal reflux in dogs by injecting inert material in the distal esophagus," Gastrointestinal Endoscopy, vol. 30, No. 5, 1984, pp. 275-280.

Shafik, "Intraesophageal Polytef injection for the treatment of reflux esophagitis," Surgical Endoscopy, 1996, vol. 10, pp. 329-331.

The BBI Newsletter, Jul. 2002, p. 192.

* cited by examiner

METHOD OF MODIFYING A LOWER ESOPHAGUS

REFERENCE TO RELATED APPLICATION

This application is a continuation-in-part of U.S. patent application Ser. No. 10/084,240, filed on Feb. 27, 2002 now abandoned, and entitled "Apparatus and Method to Inject Bulking Agent into Soft Tissue."

BACKGROUND

Gastroesophageal reflux disease, or GERD, is a medical condition caused by the repeated backup or regurgitation of food and digestive fluid from the stomach into the esophagus. The most common symptoms suggestive of GERD are heartburn or acid indigestion. GERD can damage esophageal tissues, raising the risk of serious problems such as cancer of the esophagus. It is estimated that ten percent of Americans suffer from GERD on a daily basis.

GERD occurs when a small ring of muscles called the lower esophageal sphincter ("LES") do not function properly. For example, at rest, the LES may maintain a high-pressure zone between 10 and 30 mm Hg above intragastric pressure. However, some patients suffering from GERD have an LES closing pressure of only 5 mm Hg. A weak or malfunctioning LES allows acidic stomach contents to back up into the esophagus. As the stomach contents flow back into the esophagus, the lining of the esophagus becomes irritated, creating a burning feeling in the chest. Left untreated, GERD can lead to frequent heartburn, difficulty swallowing, coughing, hoarseness, and more serious complications, such as narrowing of the esophagus, bleeding and a pre-cancerous condition called Barrett's esophagus.

There are a variety of treatments for GERD. The most common treatment involves lifestyle changes. For example, smoking, drinking, obesity, overeating, and diets high in fat and coffee all increase the chances of contracting GERD. There are also a wide variety of drugs that treat the symptoms associated with GERD. For example, antacids neutralize excess acid in the stomach to reduce irritation of the esophagus. H-2 receptor blockers reduce the amount of digestive acid that the body produces. An example of a relatively new class of drugs are Proton Pump Inhibitors that reduce acid production by affecting the final pathway of gastric acid secretion. Another class of drugs are Prokinetic agents, which treat GERD by shortening the digestion time and tightening the pressure that the LES places on the esophagus. Unfortunately, many of these drugs come with side effects, including nausea, constipation, diarrhea, cramps and potentially harmful interactions with other medications. Further, most of these medications do not treat the underlying cause of GERD, a malfunctioning LES.

Although the above treatments may be successful for some patients, surgery may be considered if relief is not obtained. The aim of surgery is often to restore the function of the LES to close during digestion. One example of a surgical procedure is laparoscopic fundoplication. After expanding the abdomen with gas, a surgeon inserts a laparoscope through an incision. Attached is a small camera that projects an internal image onto a monitor. Using this image, the surgeon reinforces the LES by wrapping the upper portion of the stomach around the lower portion of the esophagus.

An alternative to surgery has recently gained recognition, in which the submucosal layer of the lower esophagus is augmented with one of a variety of implant materials, including polytetrafluoro-ethylene (PTFE) pastes and collagen gels. For example, Rupp, "Endoscopic Antireflux Techniques," reports GERD treatments in which PTFE, collagen and hylan gel were injected into the submucosal layer of the lower esophagus. Shafik, "Intraesophageal Poltytef Injection for the Treatment of Reflux Esophagitis" and "Tissue Reaction to PTFE Pastes—A Review of the Literature," also report GERD treatments in which PTFE was injected into submucosal lower esophageal tissue sites. However, Rupp, Shafik and the Literature review report problems with PTFE pastes, including migration from the injection site and granuloma response at injection and migration sites. Thus, there is a need in the art for a method of augmenting submucosal tissue sites of the lower esophagus using PTFE-free particulate matter.

SUMMARY OF THE INVENTION

In one embodiment, the present invention provides a method of modifying the lower esophagus by injecting biocompatible PTFE-free particles suspended in a biocompatible carrier into a lower esophagus submucosal tissue site. The particles may be injected at one or more submucosal tissue sites in the vicinity of the lower esophageal sphincter.

In another embodiment, the present invention provides a method of modifying the lower esophagus by injecting biocompatible particles having an average transverse cross-sectional dimension greater than 100 microns suspended in a biocompatible carrier into a lower esophagus submucosal tissue site. The particles may be injected at one or more submucosal tissue sites in the vicinity of the lower esophageal sphincter.

In a further embodiment, the present invention provides a method for treating gastroesophageal reflux disease, or GERD. A tissue modifier composed of biocompatible PTFE-free particles suspended in a biocompatible carrier is injected into a submucosal tissue site of a patient's lower esophagus. The tissue site may be adjacent to, or in the vicinity of, the lower esophageal sphincter, or LES. Once injected, the particles may modify or bulk the esophagus to improve, enhance or optimize the functionality or competency of the LES. For example, the injected modifier may elevate the LES closing pressure to above about 15 mm HG, more particularly to between about 20 mm and 30 mm Hg.

The present invention possesses performance characteristics not apparent with other GERD treatments. For example, unlike common drug treatments, the method of the present invention may avoid drug side effects and drug interactions. Further, the method of injecting the modifier is less invasive and/or traumatic than surgical methods such as fundoplication. Further yet, the modifier is injected into the submucosal layer of the esophagus, which may provide better results than injections into the muscular layers of the esophagus. Still further, the PTFE-free embodiments of the present invention may be more biocompatible than the PTFE pastes traditionally used in submucosal injections.

DETAILED DESCRIPTION OF THE INVENTION

The present invention provides a method of modifying the lower esophagus by injecting a modifier into a submucosal tissue site of the lower esophagus. The injectable modifier includes biocompatible PTFE-free particles and a biocompatible carrier. The present invention may be used to treat gastroesophageal reflux disease, or GERD.

The esophagus is a muscular, collapsible tube that lies behind the trachea. The esophagus is about 23 to 25 cm long and begins at the end of the laryngopharynx, passes through the vertebral column, pierces the diaphragm and terminates in the superior portion of the stomach. During the esophageal stage of swallowing, food is pushed through the esophagus by involuntary muscular movements called peristalsis. Just above the level of the diaphragm, the esophagus is slightly narrowed. This narrowing has been attributed to a physiological sphincter in the inferior part of the esophagus known as the lower esophageal sphincter, or LES. The LES relaxes during swallowing and thus aids the passage of food from the esophagus into the stomach. After food has entered the stomach, a normally functioning LES acts like a valve to prevent reflux or return of the stomach contents into the lower esophagus.

The esophagus is composed of four layers of tissue, the mucosa, the submucosa, the muscularis, and the serosa. The mucosa, or inner lining of the esophagus is a mucous membrane attached to a thin layer of visceral muscle. The submucosa consists of loose connective tissue that binds the mucosa to the muscularis. The submucosa is highly vascular and is important in controlling the secretion of the GI tract. The muscularis consists of smooth muscle that is generally found in two sheets: an inner ring of circular fibers and an outer sheet of longitudinal fibers. The serosa is a serous membrane composed of connective tissue and epithelium.

In one embodiment, the method of the present invention may be used to treat gastroesophageal reflux disease, or GERD. In this embodiment, the modifier may be injected within the submucosal layer of the esophagus, or at the interface of adjacent tissue planes between the mucosa and the submucosa.

In another embodiment, the modifier of the present invention may be injected into a submucosal tissue site that extends across, or is closely adjacent to, the LES to optimize residual LES activity and to enhance any residual closing pressure of the LES. More particularly, the modifier may be injected into the submucosal esophageal folds of the lower esophagus to thicken the folds, resulting in their closer approximation within the lower esophagus. When the LES is in an open or relaxed state, the modifier allows food and liquid to pass through the esophagus. However, when the LES closes, the modifier increases the closing pressure along a sufficient axial length that, in cooperation with the contraction of the LES, it inhibits or prevents reflux of stomach contents. For example, in one embodiment, the injected modifier may increase the LES closing pressure from below about 16 mm Hg to about 18 to 30 mm Hg. In this manner, the modifier of the present invention acts as a valve-like mechanism in the esophagus when injected in the vicinity of the LES.

The precise positioning of the modifier relative to the LES depends largely on a patient's anatomy and the severity of the GERD. Depending on the degree of LES dysfunction, the modifier may be injected into a plurality of discrete submucosal tissue sites adjacent to, or in the vicinity of, the LES. In one embodiment, the modifier may be injected into two tissue sites on opposing sides of the lower esophagus. In another embodiment, the modifier may be injected circumferentially into a plurality of discrete tissue sites to modify the tissue around the LES. These embodiments may allow the esophagus to expand rapidly to permit food passage because the modifier is not connected between discrete sites. In an alternate embodiment, the modifier may be injected into the submucosal layer in the form of a continuous or discontinuous ring or mass around the esophagus.

In yet another embodiment, the present method may enhance or increase the competency of the valve-like function of the LES. After food has passed through the esophagus and entered the stomach, the stomach distends, causing the mucosal layer of the esophagus to stretch and slide into the stomach relative to the muscular layer.

This downward longitudinal movement of the mucosa not only causes the mucosa to be more tightly apposed in the vicinity of the LES (and the modifier), but also results in a downward and inward rotation of the modifier. This, in turn, pulls inwardly the muscle layers to enhance the valve-like function of the modifier. Thus, embodiments of the present invention may react to increasing pressure or distension in the stomach by enhancing or increasing the competency of the inhibiting function of the LES.

Almost any suitable PTFE-free biocompatible particle may be used in accordance with the present invention. In one embodiment, the particles or particulate material are generally made of a durable biocompatible material, for example, a ceramic such as zirconium or aluminum oxide, gold, titanium, silver, stainless steel, graphite, isotropic pyrolytic carbon, oxides, PTFE-free polymers, metal alloys and/or combinations thereof. In other embodiments, the particles may be carbon coated particulate substrates. Suitable particulate substrates generally include particles capable of accepting a carbon coating, such as the particles or particulate material described above. The particulate substrates may be carbon coated, for example, with pyrolytic carbon, vitreous carbon, diamond-like carbon or graphite by conventional techniques. Optionally, the particulate substrate may be radiopaque. In one embodiment, the particles include isotropic pyrolytic carbon coated onto a graphite or ceramic particulate substrate. The atomic structure of pyrolytic and vitreous carbon is similar to graphite, but the alignment between hexagonal planes of atoms is not as well ordered as in graphite. Pyrolytic carbon is characterized by a more chaotic atomic structure and better bonding between layer planes. The carbon coating provides a relatively smooth surface for injection into a tissue site.

Pyrolytic carbon may be produced and coated onto particulate substrate surfaces by known methods. In one technique, hydrocarbons and alloying gases are decomposed to prepare a pyrolytic carbon coating on the particulate substrates. The particulate substrates are contacted with the hydrocarbons and alloying gases in a fluidized or floating bed at a temperature sufficient to cause deposition of pyrolyzed carbon onto the particulate substrate surfaces, typically from about 1200 to 1500°. Inert gas flow is used to float the bed of particulate substrates, optionally including an inert mixing media. The hydrocarbon pyrolysis results in a high carbon, low hydrogen content carbon material being deposited as a solid layer of material onto the particulate substrates.

Alternatively, a carbon coating (sometimes referred to as "ultra-low-temperature isotropic carbon") may be applied to particulate substrates using any one of other various coating processes for depositing carbon, such as a vacuum vapor deposition process. Such a method uses ion beams generated from any of a variety of known processes, such as the dissassociation of $CO_2$, reactive dissociation in vacuum of a hydrocarbon as a result of a glow discharge, sublimation of a solid graphite source, or cathode sputtering of a graphite source. Gold has been found to be an especially suitable particulate substrate for vacuum vapor deposited carbon. Other particulate substrates, including but not limited to nickel, silver, stainless steel, zirconium, graphite or titanium are also quite acceptable for this type of coating process.

Isotropic carbon may also be applied to temperature-sensitive substrates using physical vapor depositions techniques. Physical vapor deposition involves transferring groups of carbon atoms from a pyrolytic carbon target to a desired substrate at low temperatures. The process may be carried our in high-vacuum conditions to prevent chemical reaction. This technique may be suitable for coating a variety of substrates such as temperature-sensitive polymers and metal alloys.

The high strength, resistance to breakdown or corrosion, and durability of a coated carbon surface ensures effective, long term functioning of coated particles in tissue modifying applications. The established biocompatibility of carbon coatings such as pyrolytic and vitreous carbon coatings makes the described particles particularly suitable for tissue modifying applications. The particulate substrates may be completely encased by a carbon surface. This results in a uniformly coated particle with no substrate exposure on the surface of the particle. Preferred carbon coatings may be in the range of fractions of thousandths of an inch, e.g., about one half of a thousands of an inch (0.0005 inches), on average, covering the surface of the particle substrate.

The particles, whether coated or uncoated, are preferably shaped and sized to provide enhanced passage through a hypodermic needle, while substantially remaining at the tissue site once injected. The shape and size of the injected particles may be varied to enhance the flow of the particles during injection. However, if the particles are too small, they can be engulfed by the body's white cells (phagocytes) and carried to distant organs or be carried away in the body's microvasculature system and travel until they reach a site of sufficient constriction to prevent further movement. The particles may range in size from 10 microns to 1,000 microns in average, transverse cross-sectional dimension, more particularly between 100 and 300 microns. The particles may be subjected to a cleaning, polishing and sieving process to remove contaminants, smooth the particle surface to a desired texture and to separate out particles of a size less than or greater than a desired size range.

The biocompatible particles are delivered to the tissue site in a suitable biocompatible carrier. Any biocompatible carrier that can deliver the particles to a tissue site may be used in accordance with the present invention. A carrier may be a biologically compatible solution. Examples of suitable carriers include solutions containing glucan, collagen, saline, dextrans, glycerol, polyethylene glycol, corn oil or safflower, other polysaccharides or biocompatible polymers, methyl cellulose, agarose, or combinations thereof. In certain embodiments, a curable polymer such as PMMA may be added to the carrier to provide additional stiffening characteristics. The viscosity of the carrier ranges between about 10 and 75,000 centipoise.

Solutions containing β-glucan and collagen are particularly suitable carriers for the present invention. β-glucan is a naturally occurring constituent of cell walls in essentially all living systems including plants, yeast, bacteria, and mammalian systems. Its effects and modulating actions on living systems have been reported by Abel et. al., "Stimulation of Human Monocyte B-glucan Receptors by Glucan Particles Induces Production of TNF-∂ and 1L-B," Int. J. Immunopharmacol., 14(8):1363-1373, 1992. β-glucan, when administered in experimental studies, elicits and augments host defense mechanisms including the steps required to promote healing, thereby stimulating the reparative processes in the host system. β-glucan is removed from tissue sites through macrophagic phagocytosis or by enzymatic destruction by serous enzymes. The destruction or removal of β-glucan, as well as its available viscosity and lubricous nature, make it a useful carrier for the particles in tissue modifying applications.

Aqueous solutions of β-glucan may be produced that have favorable physical characteristics as a carrier for particles in tissue modifying applications. The viscosity can vary from a thin liquid to a firm, self-supporting gel. Irrespective of viscosity, the β-glucan solution has excellent lubricity, thereby creating a particle-carrier composition which is easily administered by delivery to a predetermined body site through a small bore needle. Useful β-glucan compositions include β-D-glucans containing 4-0-linked-β-D-glycopyranosyl units and 3-0-linked-β-D-glycopyranosyl units, or 5-0-linked-β-D-glycopyranosyl units and 3-0-linked-β-D-glycopyranosyl units. The carrier may be of sufficient viscosity to assure that the particles remain suspended therein, for a sufficient time duration to accomplish the injection procedure.

Collagen, another suitable carrier, is a naturally occurring protein that provides support to various parts of the human body, including the skin, joints, bone and ligaments. One suitable injectable collagen manufactured by the McGhan Medical Corporation, Santa Barbara, Calif., and sold under the trade names ZYDERM and ZYPLAST, is derived from purified bovine collagen. The purification process results in a product similar to human collagen. Collagen solutions may be produced within a wide viscosity range to meet an individual patient's needs, and mixed with the particulate material for injection into a patient.

Another example of a suitable carrier material is a solution containing methyl cellulose or another linear unbranched polysaccharide. Further examples of appropriate carrier materials include agarose, hyaluronic acid, polyvinyl pyrrolidone or a hydrogel derivative thereof, dextran or a hydrogel derivative thereof, glycerol, polyethylene glycol, oil-based emulsions such as corn or safflower, or other polysaccharides or biocompatible organic polymers either singly or in combination with one or more of the above-referenced solutions.

The amount of particles in the modifier may be any amount that will provide a modifier that is flowable and injectable, and that will allow a desired amount of particles to be delivered to a tissue site. Amounts of particles in the tissue modifier can be in the range from about 5 to 85 percent by volume, more particularly from about 20 to 60 percent by volume, and most particularly from about 30 to 50 percent by volume.

In use, the modifier will typically be injected as a slurry, suspension, or emulsion, through a needle, into a tissue site. When deposited into a tissue site, the carrier may be carried away into the body and then be dispersed or degraded. It is preferred that some of the particles are substantially immobile upon delivery to a tissue site for modification. Particles used for tissue modifying according to the invention may be sufficiently immobile to be used for substantially permanent tissue modifying applications. If the particles tend to move at all after delivery to a tissue site, the particles generally will do so only along the path of the needle that was used to inject them.

The modifier may be delivered to a tissue site using any instrument or apparatus that can be used to inject an amount of particles, preferably contained or suspended in a carrier, through the skin or mucosa, to a desired submucosal tissue site in the lower esophagus. In one embodiment, a suitable apparatus or medical device includes a probe having an optical viewing device. A conventional or other suitable gastroscope or endoscope can be used as the probe. A needle assembly may be carried by the probe for injecting the modifier. A conventional syringe may also be used to introduce the modifier into the needle. Optionally, two or more additional syringes may be employed for delivering other biocompatible solutions such as saline. The particular instrument used for delivery is not critical, provided that its components are compatible with the modifier.

In one embodiment, a distal end of the probe may be introduced through the mouth of the patient and down the esophagus to the vicinity of the tissue site to be treated. The optical viewing device assists a surgeon in advancing the probe. The needle is then introduced through the probe and advanced to the vicinity of the distal end of the probe. Under the guidance of the optical viewing device, the probe is maneuvered to a position above the portion of tissue to be treated. For example, the probe may be maneuvered to a location adjacent to, or in the vicinity of, the lower esophageal sphincter.

The needle is then inserted into or between selected tissue planes, such as the mucosal or submucosal layers. Optionally, in one embodiment of the present invention, a biocompatible liquid such as saline may be first injected into the tissue plane to provide an enlarged cavity for injecting the modifier. The amount of injected liquid may range from 0.25 to 10 cc. The needle is then retracted and cleansed of the biocompatible liquid.

The needle may then be primed with the modifier and reinserted into or between the desired tissue layer. Thereafter, a predetermined amount of modifier is slowly injected through the needle to the tissue site. In detectable embodiments, the modifier may be monitored during and after injection to ensure proper placement.

In another embodiment, the apparatus reported in U.S. patent application Ser. No. 10/084,240, incorporated herein by reference, may be used to deliver embodiments of the present invention. The reported apparatus includes a syringe and a hypodermic needle having both linear and arcuate segments. The hypodermic needle is sufficiently rigid so as to maintain both the linear and arcuate segments, but retains a minimal amount of flexure to aide in the proper insertion and positioning of the needle into tissue.

The amount of particles introduced to modify the tissue can be any amount sufficient to modify the tissue site as desired. The amount delivered can vary depending on factors such as the size of the particles, the extent of necessary modification, the tissue condition to be treated and other factors particular to specific patients. Such factors will be within the skill of an artisan of ordinary skill in the medical arts, and such an artisan will be able to understand what is a useful amount of particles for delivery to lower esophagus tissue sites.

One characteristic of the modifier of the present invention is that it may be injected into tissue in incremental portions. In this manner, only the minimally necessary amount of modifier is added. This drastically reduces the possibility that the functionality of the esophagus will be adversely affected by the modifier. In certain embodiments, the modifier may include detectable, preferably radiopaque, particles. In these embodiments, the injected modifier may be viewed during or after the procedure to determine the location of the particles within the tissue, and the overall effect of the modifiers. If, after a first injection, the tissue is not sufficiently modified, precise amounts of additional modifier may be injected into the tissue site. The present invention may also be injected into a plurality of discrete tissue sites to modify the lower esophagus as desired.

This invention is not to be taken as limited to all of the details described above as modifications and variations thereof may be made without departing from the spirit or scope of the invention.

What is claimed is:

1. A method of modifying a lower esophagus of a patient comprising injecting an effective amount of a modifier comprising biocompatible carbon coated particles having an average transverse cross-section dimension of between about 80 and about 300 microns and a biocompatible carrier into a plurality of discrete tissue sites within the submucosal layer of the esophagus in the vicinity of a lower esophageal sphincter of the patient.

2. The method of claim 1 wherein the biocompatible particles comprise carbon coated ceramic particles.

3. The method of claim 1 wherein the biocompatible particles comprise carbon coated zirconium oxide particles.

4. The method of claim 1 wherein the carbon coating comprises isotropic pyrolytic carbon.

5. The method of claim 1 wherein the biocompatible particles comprise isotropic pyrolytic carbon coated zirconium oxide.

6. The method of claim 1 wherein the biocompatible particles comprise isotropic pyrolytic carbon coated graphite.

7. The method of claim 1 wherein the biocompatible particles comprise isotropic pyrolytic carbon coated polymer particles.

8. The method of claim 1 wherein the biocompatible carrier is a liquid or a gel.

9. The method of claim 1 wherein the biocompatible carrier includes β-glucan or collagen.

10. The method of claim 1 wherein the modifier has a viscosity of between about 10 and 75,000 centipoise.

11. The method of claim 1 wherein the modifier comprises about 5 to 85 v/v percent biocompatible particles.

12. The method of claim 1 wherein the modifier comprises about 20 to 60 v/v percent biocompatible particles.

13. The method of claim 1 wherein the modifier comprises about 30 to 50 v/v percent biocompatible particles.

14. The method of claim 1 further comprising the step of detecting the biocompatible particles.

15. The method of claim 14 wherein the detecting step occurs during the injecting step.

16. The method of claim 1 further comprising injecting a biocompatible liquid into the submucosal tissue site to provide an internal space for injecting the modifier.

17. The method of claim 1 wherein a tissue site within the submucosal layer comprises an esophageal fold of the lower esophagus.

18. The method of claim 1 wherein the plurality of discrete tissue sites within the submucosal layer comprise a plurality of esophageal folds of the lower esophagus.

19. The method of claim 1 wherein the plurality of discrete tissue sites within the submucosal layer are circumferentially disposed around the lower esophagus.

20. The method of claim 1 further comprising injecting an additional amount of modifier into the a tissue site within the submucosal layer.

* * * * *